Figure 1:
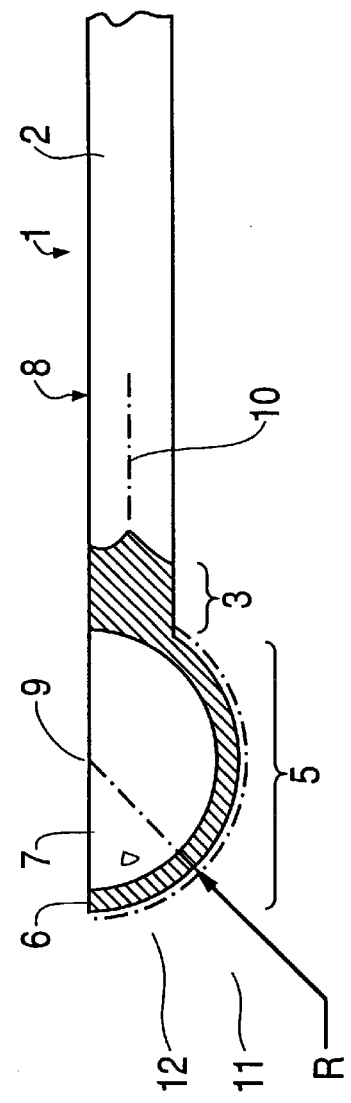

United States Patent [19]
Vanraes

[11] Patent Number: 5,897,568
[45] Date of Patent: Apr. 27, 1999

[54] DEVICE PARTICULARLY INTENDED FOR THE HYGIENE OF THE AUDITORY MEATUS

[76] Inventor: Pierre Vanraes, 54-56 rue de Gand, 59200 Tourcoing, France

[21] Appl. No.: 08/142,381
[22] PCT Filed: May 21, 1992
[86] PCT No.: PCT/FR92/00456
§ 371 Date: Nov. 29, 1993
§ 102(e) Date: Nov. 29, 1993
[87] PCT Pub. No.: WO92/21308
PCT Pub. Date: Dec. 10, 1992

[30] Foreign Application Priority Data

May 31, 1991 [FR] France .................................. 91 06835

[51] Int. Cl.⁶ .............................. A61F 9/00; A61B 17/22
[52] U.S. Cl. ............................................ 606/162; 606/160
[58] Field of Search ............................... 606/1, 106, 131, 606/160–162; 73/426; 30/128, 141, 147, 149, 150, 324

[56] References Cited

U.S. PATENT DOCUMENTS

| | | | |
|---|---|---|---|
| 155,790 | 10/1874 | Clark | 606/162 |
| 896,338 | 8/1908 | Tolman | 606/131 |
| 1,468,894 | 9/1923 | Zajicek | 606/160 |
| 1,672,816 | 6/1928 | Kohr . | |
| 2,617,420 | 11/1952 | Jozefczyk | 606/161 |
| 3,110,304 | 11/1963 | Hartman | 128/9 |

FOREIGN PATENT DOCUMENTS

| | | | |
|---|---|---|---|
| 2277557 | 2/1976 | France . | |
| 2551657 | 3/1985 | France . | |
| 0571401 | 3/1933 | Germany | 73/426 |
| 1188775 | 3/1965 | Germany | 606/161 |

*Primary Examiner*—Glenn K. Dawson
*Attorney, Agent, or Firm*—Kerkam, Stowell, Kondracki & Clarke; Dennis P. Clarke

[57] ABSTRACT

The invention relates to a device for so called auricular hygiene since it is particularly intended for the hygiene of the auditory meatus of persons, which device is comprised of a cylindrical body (2) having two opposite extremities (3, 4), of which at least one carries, particularly without any blend, an active part (5) which is itself comprised of a substantially circular active edge (6) to detach material from a predetermined surface and also a depression or cavity (7) to collect said material. It is characterized in that each active part (5) is configured like a semi-spherical envelope having a predetermined radius (R).

5 Claims, 1 Drawing Sheet

DEVICE PARTICULARLY INTENDED FOR THE HYGIENE OF THE AUDITORY MEATUS

The invention relates to a device, particularly intended for the hygiene of human auditory canals.

More especially, the invention relates to a device of the type mentioned, which includes an elongated body of substantially cylindrical shape having two extremities, at least one of which, generally without any break in continuity, has an active hollow portion intended for collecting a material such as ear wax.

In the devices in the prior art, such as those described in the references (U.S. Pat. No. 1,672,816, French Patent Disclosure 2.277.557 A, and French Patent Disclosure 2.551.657 A), the aforementioned active portion is constituted by a sort of rounded spatula that has a slight depression.

The known active portions are hence notably flat and thus constitute a kind of spoon.

The thus-equipped devices are effective, but using them is regrettably dangerous for the eardrum.

To overcome this disadvantage without altering the effectiveness of the device, it is known (French Patent Disclosure 2.277.557 A) to equip the body of this device with a stop, disposed and oriented such that in use it comes to cooperate with a natural shoulder of the auditory canal and thereby limits the engagement of the active portion in the canal.

This arrangement is effective, but it markedly increases the production cost of the device.

The essential object that the invention seeks to attain is an auricular hygiene device, which while effective and not dangerous is lower in cost than these known devices.

To that end, the subject of the invention is an auricular hygiene device, characterized in particular that each active portion has a hemispherical envelope shape of a predetermined radius.

Figure 2:
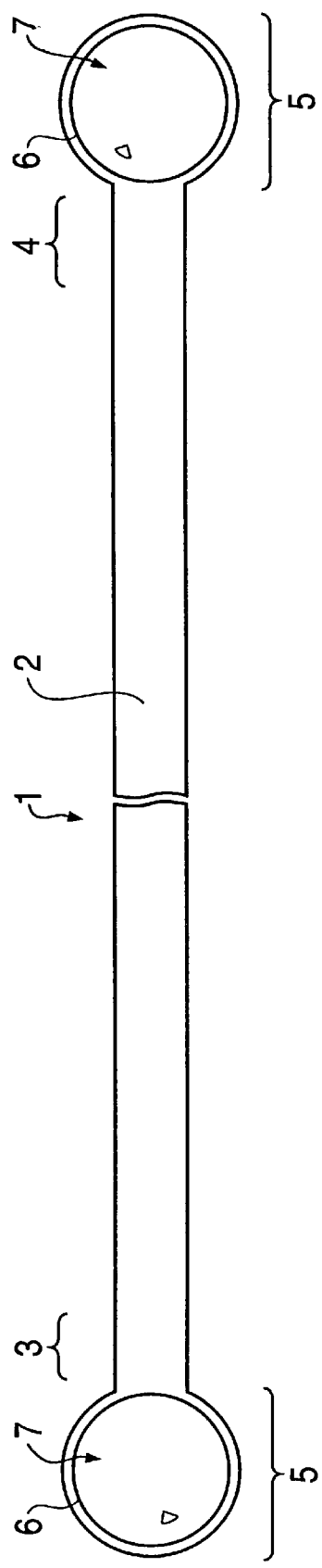

The invention will be better understood from the ensuing description, given by way of non-limiting example, in conjunction with the accompanying drawing, which schematically shows the following:

FIG. 1: a cross-sectional view on a large scale of the active portion of the device;

FIG. 2: the device of the invention, on a large scale in a full frontal view.

Turning to the drawing, one sees a device 1, called an "auricular hygiene device" because it is intended in particular for the hygiene of human auditory canals (not shown).

Classically, the device includes a cylindrical body 2 having two opposed extremities 3, 4, at least one of which, particularly without any break in continuity, has an active portion 5 that in turn includes on the one hand a substantially circular active edge 6 intended for detaching a material from a predetermined surface, and on the other a depression or cavity 7 intended for collecting this material.

As shown and as is characteristic for the invention, each active portion 5 has the shape of a spherical envelope of a predetermined radius R.

According to the invention, the substantially circular edge of the active portion 5 is located in a plane approximately at a, tangent to one of the external generatrices, that is, the generatrix marked 8, of the cylindrical body 2 that has the active portion 5.

Preferably, the cavity 7 that the hemispherical active portion includes is itself hemispherical.

According to the invention, the point of origin 9 of any radius of the active portion 5 is located approximately in a plane that contains the longitudinal axis 10 of the body 2.

Thus constituted, and however short it may be, the radius of the hemispherical active portion is chosen in such a way as to limit the engagement in the auditory canal to a predetermined value.

The device according to the invention cannot cause any injury, since the circular edge 6 of the active portion cannot be used to pick up the ear wax except by displacements at a tangent to the outer face of this active portion.

According to the invention, at least a fraction of the outer surface 11 of the active portion 5 has a flexible lining 12 that has fine irregularities, so as to catch any material or fatty substance it is put into contact with.

According to the invention, when the device is intended for use in a child, the radius of the hemispherical portion is greater than 2.25 mm.

According to the invention, when the device is intended for use in an adult, the radius of the hemispherical portion is greater than 3.35 mm.

Preferably, the body 2 of the device 1 and its active portion 5 are made of a resilient material, on the one hand, and the body 2 has a certain flexibility, on the other.

These last two parameters of construction are within the competence of one skilled in the art.

I claim:

1. An auricular hygiene device comprising external generatrices defining a cylindrical body having a longitudinal axis and two opposed extremities, at least one of which has an active portion that includes a substantially circular active edge intended for detaching a material from a predetermined surface and a depression or cavity intended for collecting said material, wherein said active portion has a hemispherical outer surface shape with a predetermined radius and wherein the point of origin of any radius of the active portion is located approximately in a plane that contains the longitudinal axis of the cylindrical body.

2. The device of claim 1, wherein the substantially circular edge of the active portion is located in a plane approximately at a tangent to one of the external generatrices defining the cylindrical body that carries said active portion.

3. The device of claim 1, wherein at least a fraction of the outer surface of the active portion has a flexible lining that has fine irregularities for catching any material or fatty substance that the flexible lining comes into contact with.

4. The device of claim 3, wherein, the device is intended for use in a child, and predetermined radius of the hemispherical outer surface is greater than 2.25 mm.

5. The device of claim 3, wherein, the device is intended for use in an adult, and predetermined radius of the hemispherical outer surface is greater than 3.35 mm.

* * * * *

UNITED STATES PATENT AND TRADEMARK OFFICE
CERTIFICATE OF CORRECTION

PATENT NO : 5,897,569
DATED : April 27, 1999
INVENTOR(S) : Pierre Vanraes

It is certified that error appears in the above-identified patent and that said Letters Patent is hereby corrected as shown below:

Please delete the Abstract in its entirety and replace therefor the following:

--A device for the hygiene of the auditory meatus includes a cylindrical body having two opposed extremities of which at least one has an active part. The active part has a substantially circular active edge to detach material from the ear canal and a depression or cavity to collect the material. Each active part is configured like a semi-spherical envelope having a predetermined radius.--

Signed and Sealed this

Thirtieth Day of January, 2001

*Attest:*

Q. TODD DICKINSON

*Attesting Officer*     *Director of Patents and Trademarks*